(12) United States Patent
Baron

(10) Patent No.: US 6,558,711 B1
(45) Date of Patent: May 6, 2003

(54) COMPOSITION AND METHOD FOR REDUCING THE RISK OF CARCINOGENESIS

(75) Inventor: John A. Baron, Norwich, VT (US)

(73) Assignee: The Trustees of Dartmouth College, Hanover, NH (US)

( * ) Notice: Subject to any disclaimer, the term of this patent is extended or adjusted under 35 U.S.C. 154(b) by 0 days.

(21) Appl. No.: 10/210,303

(22) Filed: Aug. 1, 2002

Related U.S. Application Data

(63) Continuation of application No. 09/819,009, filed on Mar. 27, 2001, now Pat. No. 6,488,966, which is a continuation of application No. 09/464,047, filed on Dec. 15, 1999, now Pat. No. 6,251,439.
(60) Provisional application No. 60/115,667, filed on Jan. 13, 1999, and provisional application No. 60/112,246, filed on Dec. 6, 1998.

(51) Int. Cl.[7] ............................................... A01N 59/08
(52) U.S. Cl. ........................ 424/678; 424/682; 424/686; 424/687
(58) Field of Search ................................ 424/678, 682, 424/686, 687

(56) References Cited

U.S. PATENT DOCUMENTS 4,851,221 A * 7/1989 Pak et al. .................... 424/693

OTHER PUBLICATIONS

Newmark, H.L., et al., "Colon Cancer and Dietary Fat, Phosphate and Calcium: A Hypothesis", *JNCI*, vol. 72, No. 6, pp 1323–1325, Jun. 1984.

Pence, B. et al., "Inhibition of dietary fat–promoted colon carcinogenesis in rats by supplemental calcium or vitamin $D_3$," *Carcinogenesis*, vol. 9, No., pp187–190, 1988.

Pence, B., "Role of calcium in colon cancer prevention: Experimental and clinical studies", *Mutation Research*, vol. 290, pp 87–95, 1993.

Bergsma–Kadijk, J.A., "Calcium Does Not Protect against Colorectal Neoplasia", *Epidemiology*, vol. 7, No. 6, pp 590–597, 1996.

Martinez, M.E., "Calcium, Vitamin D, and Colorectal Cancer: A Review of the Epidemiologic Evidence" *Cancer Epideminology, Biomarkers & Prevention*, vol. 7, pp 163–168, 1998.

Benito, E., et al., "Diet and Colorectal Adenomas: A Case–Control Study In Majorca" *Int. J. Cancer*, vol. 55, pp 213–219, 1993.

Macquart–Moulin, G. et al., "Colorectal Polyps and Diet: A Case–Control Study in Marseilles", *Int. J. Cancer*, vol. 40, pp 179–188, 1987.

Janerich, D.T., "Forecasting Cancer Trends to Optimize Control Strategies", *JNCI*, vol. 72, No1.6, pp 1317–1321, 1984.

Morson, B.C., "Adenomas of large bowel", *Cancer Surveys*, vol. 2, No. 3, pp 451–477, 1983.

* cited by examiner

*Primary Examiner*—James H Reamer
(74) *Attorney, Agent, or Firm*—Darby & Darby

(57) ABSTRACT

A method for promoting colon health in a subject comprising administering a dose of calcium to the subject that is effective to reduce carcinogenesis. Particularly provided is a method for reducing the risk of recurrence of colorectal adenomas, comprising administering a dose of calcium carbonate effective to promote colon health. In an example, 1200 mg of elemental calcium (supplied in 3000 mg of calcium carbonate) administered once or twice daily resulted in decreased risk of recurrent colorectal adenomas in patients with a history of colorectal adenomas.

13 Claims, No Drawings

COMPOSITION AND METHOD FOR REDUCING THE RISK OF CARCINOGENESIS

This application is a continuation of application Ser. No. 09/819,009, filed on Mar. 27, 2001 now issued U.S, Pat. No. 6,488,966, which is a continuation of application Ser. No. 09/464,047, filed Dec. 15, 1999, now issued U.S. Pat. No. 6,251,439, which claimed priority from U.S. Provisional Application Ser. No. 60/115,667, filed Jan. 13, 1999, and U.S. Provisional Application Ser. No. 60/112,246, filed Dec. 6, 1998, the disclosures of each of which are incorporated by reference herein in their entireties.

The research leading to the present invention was supported, in part, by National Institutes of Health Grants No. CA37287 and CA23108. Accordingly, the Government may have certain rights in the invention.

FIELD OF THE INVENTION

The present invention relates to reducing the risk, and optimally preventing, carcinogenesis through modification of diet. In particular, ingestion of calcium results in reduced risk of recurrence of colorectal adenomas.

BACKGROUND OF THE INVENTION

Dietary patterns have repeatedly been associated with the risk of colorectal neoplasia: a diet rich in vegetables and fruits is associated with a lower risk, while intake of animal fat and red meat seems to increase risk (Sandler, Gastroenterology Clinics NA, 25:717–735, 1996). The underlying mechanisms are not clear, but may in part be due to alterations in bile acids, which are carcinogenic in animal models (Nagengast et al., Eur. J. Cancer, 1995, 31A:1067–70).

Newmark and colleagues (Newmark et al., J. Natl. Cancer Inst., 1984, 72:1323–1325) proposed that calcium binds bile acids in the bowel lumen, inhibiting their proliferative and carcinogenic effects. In support of this hypothesis, animal studies have indicated a protective effect of dietary calcium on bile-induced mucosal damage and experimental bowel carcinogenesis (Pence, Mut. Res., 1993, 290:87–95; Pence, Carcinogenesis, 1988, 9:187–190). However, human epidemiological research has been inconsistent; in some studies a decreased risk of colorectal cancer has been associated with calcium intake, while in others, no association was found (Blergsma-Kadijk et al., Epidemiology, 1996, 7:590–597; Martinez and Willett, Cancer Epidemiol. Biomarkers Prev., 1998, 7:163–168). Similarly mixed results have been reported regarding large bowel adenomas, likely precursors for most colorectal cancers (Morson et al., Cancer Surv., 1983, 2:451–477).

SUMMARY OF THE INVENTION

The present invention advantageously provides a method for reducing a risk of carcinogenesis in a subject comprising administering a dose of calcium to the subject that is effective to reduce carcinogenesis. Particularly provided is a method for reducing the risk of recurrence of colorectal adenomas, comprising administering a dose of calcium carbonate effective to reduce the risk of colorectal adenomas.

DETAILED DESCRIPTION OF THE INVENTION

In its broadest aspect, the present invention provides a method for reducing a risk of carcinogenesis in a subject comprising administering a dose of calcium to the subject that is effective to reduce carcinogenesis. Preferably, the carcinogenesis is development of a colorectal adenoma, e.g., a recurrence of an adenoma. Thus, in a specific embodiment, the method provides for reducing the risk of recurrence of colorectal adenomas, comprising administering a dose of calcium carbonate effective to reduce the risk of colorectal adenomas.

More particularly, the present invention is able to reduce the risk ratio of adenoma recurrence, resulting in a risk ratio of 0.74 to 0.98, e.g., about 0.85, with a 95% confidence interval. Indeed, as demonstrated in the Example, infra, the risk ratio of at least one adenoma was by 0.67 to 0.99, e.g., about 0.81, with a 95% confidence interval.

The effective dose of elemental calcium can be readily established. In particular, a dose ranging from about 1 mg/kg/day to about 100 mg/kg/day, preferably from about 1 mg/kg/day to about 50 mg/kg/day, and more preferably about 20 mg/kg twice a day, can be used. In a specific embodiment, the dose of elemental calcium is about 1200 mg twice a day.

Elemental calcium can be derived from many sources. Usually, it is found in a salt. Examples of calcium sources include, but are by no means limited to, calcium carbonate, calcium citrate, calcium hydroxide, calcium phosphate (including tricalcium phosphate and dicalcium phosphate), calcium chlorophosphate, or combinations thereof. In a specific embodiment, the calcium is provided as calcium carbonate.

When calcium carbonate is administered to the subject, a preferred dose is from about 20 to about 80 mg/kg twice a day, and more preferably about 40 mg/kg twice a day. In a specific embodiment, the dose is about 3000 mg twice a day.

The present invention is based, in part, on the discovery that 1200 mg of elemental calcium (supplied in 3000 mg of calcium carbonate) administered twice daily resulted in decreased risk of recurrent colorectal adenomas in patients with a history of colorectal adenomas. In particular, 930 patients with a recent history of colorectal adenomas were randomized to calcium carbonate (3 gm daily; 1,200 mg elemental calcium) or placebo, with follow-up colonoscopies one and four years after the qualifying examination. The main analysis focused on new adenomas found after the first follow-up endoscopy, up to (and including) the second follow-up examination. Risk ratios of at least one recurrent adenoma and ratios of the average numbers of adenomas and 95% confidence intervals were calculated as measures of effect.

As a result of this treatment protocol, there was a lower risk of recurrent adenomas in subjects randomized to calcium. Among the 913 subjects who had at least one study examination, the adjusted risk ratio of any adenoma recurrence was 0.85 (95% confidence interval 0.74 to 0.98; P=0.03). 832 patients completed both follow-up examinations and so were included in the main analysis; the adjusted risk ratio of at least one adenoma was 0.81 (95% confidence interval 0.67 to 0.99; P=0.04); the adjusted ratio of the average numbers of adenomas was 0.76 (95% confidence interval 0.60 to 0.96; P=0.02). The effect of calcium was independent of initial dietary fat and calcium intake. No toxicity was associated with supplementation. These findings indicate that calcium supplementation can prevent a proportion of colorectal adenomas, precursors of most colorectal cancers.

As used herein, the term "carcinogenesis" refers to the development of a carcinoma, particularly an adenocarcinoma of the colon or rectum. In a specific embodiment, carcinogenesis refers to development of an adenoma. In more specific embodiment, carcinogenesis refers to recurrent adenomas.

In a specific embodiment, the term "about" or "approximately" means within 20%, preferably within 10%, and more preferably within 5% of a given value or range.

The various elements of the invention are further elaborated in the following sections concerning carcinomas, calcium sources, formulations, and administration. These sections are provided for the sake of convenience, and are not intended to limit the scope of the invention.

Carcinomas

A carcinoma is malignant new growth that arises from epithelium, found in skin or, more commonly, the lining of body organs, for example: breast, prostate, lung, stomach or bowel. Carcinomas tend to infiltrate into adjacent tissue and spread (metastasize) to distant organs, for example: to bone, liver, lung or the brain. An adenocarcinoma is a form of cancer that involves cells from the lining of the walls of many different organs of the body. Colorectal cancer is a type of adenocarcinoma. While the present invention focuses on carcinogenesis of the lower intestinal tract, it is believed to impact carcinogenesis broadly. Thus, though the application focuses on carcinogenesis in colorectal cancer (or carcinoma or adenocarcinoma), it should be generally considered as relating to carcinogenesis in general.

Colorectal cancer is a malignancy that arises from the lining of either the colon or the rectum. Cancers of the large intestine are the second most common form of cancer found in males and females. Symptoms include rectal bleeding, occult blood in stools, bowel obstruction and weight loss. Treatment is based largely on the extent of cancer penetration into the intestinal wall. Surgical cures are possible if the malignancy is confined to the intestine. The risk can be reduced when following a diet which is low in fat and high in fiber.

As used herein, a polyp is a growth, usually benign, protruding from a mucous membrane. Colorectal polyps can be precursors to carcinomas.

Surgery is the primary method of treatment for polyp removal and the treatment of colorectal cancer. The extent of surgery and the need for follow-up treatment afterwards (with chemotherapy or radiation) depends on the stage of the disease as well as its location—whether it is in the colon or rectum. Information regarding staging and treatment provided separately for each disease below.

Colon Cancer Staging

There are three slightly different systems for staging colon cancer: Dukes, Astler-Coller and AJC/TNM. The list below describes each stage using the AJC/TNM system with the corresponding stage for Dukes and Astler-Coller noted afterward, as well as the recommendation for treatment in addition to surgery.

Stage O: Carcinoma in situ. Cancer is confined to the inner layer of the colon. There is no corresponding stage for Dukes or Astler-Coller. No treatment after surgery or polypectomy. The survival rate approaches 100 percent.

Stage I: Cancer has grown through the inner lining of the colon and underlying layers, but has not penetrated beyond the colon wall into adjoining tissue. This stage corresponds to Dukes Stage A and Astler-Coller Stages A and B1. No treatment after surgery. The survival rate is about 90 percent.

Stage II: Cancer has grown entirely through the colon wall but hasn't spread to nearby lymph nodes. The stage corresponds to Dukes Stage B and to Astler-Coller Stages B2 and B3. Treatment is usually surgery alone. In some cases, chemotherapy may be offered. The survival rate is about 70 percent.

Stage III: Cancer has spread to nearby lymph nodes but not to other parts of the body. The stage corresponds to Dukes Stage C and to Astler-Coller Stages C1, C2 and C3. After surgery, treatment with chemotherapy is recommended. The survival rate is 35 percent to 65 percent.

Stage IV: Cancer has spread to distant organs. Most common sites for metastasis are the liver, lungs and brain. There is no corresponding Dukes stage; the Astler-Coller Stage is D. Treatment after surgery consists of chemotherapy, radiation therapy or both to relieve symptoms of advanced cancer. Occasionally, surgery can be performed on the metastasis. The survival rate is 8 percent.

Rectal Cancer Staging

As with colon cancer, treatment for rectal cancer depends on the stage of the disease.

Stage O: Cancer has not grown beyond the rectal lining. There is no treatment after surgery, and the survival rate is greater than 90 percent.

Stage I: Cancer has penetrated the inner rectal lines, but not beyond. Chemotherapy and radiation is not usually recommended after surgery. The survival rate is about 88 percent.

Stage II: Cancer has penetrated through the rectal wall but hasn't spread to the lymph nodes. Treatment often includes surgery combined with chemotherapy and radiation. The survival rate is 65 percent to 75 percent.

Stage III: Cancer has spread to nearby lymph nodes but not to other parts of the body. Surgery is usually combined with chemotherapy and radiation which can be given either before or after the operation. The survival rate is between 35 and 55 percent.

Stage IV: Cancer has spread to distant organs. Most common sites for metastasis is the liver. The goal of surgery is not to cure cancer but to relieve symptoms and prevent blockage of the rectum. Chemotherapy, radiation or both may be recommended to relieve symptoms. The survival rate is 5 percent. In some cases, isolated metastasis, particularly to the liver, can be surgically removed, resulting in improved survival.

Treatment of Colorectal Cancer

Treatment of rectal cancer often combines surgery with chemotherapy and radiation, depending on the stage of the disease (see colon cancer treatment for discussion of these treatments). Sometimes surgery is performed first, and on other occasions, chemoradiation is given prior to surgery. A number different surgical procedures are available to treat rectal cancer, the choice depending on the location and stage of the cancer. These include polypectomy (removal of Stage 0 tumors), local excision, low anterior resection, abdominoperineal resection; and pelvic exenteration; which is only rarely performed.

Either after or before surgery, radiation therapy may be recommended for rectal cancer. When given before surgery, the tumor can be shrunk, often making removal easier. Radiation therapy is rarely recommended for cancer of the colon. Treatment usually is done on an outpatient basis and involves five sessions per week for approximately six weeks. Radiation treatment can cause a number of side effects, including upset stomach, diarrhea, fatigue and skin irritation, which subside once treatment ends.

Treatment with anti-cancer drugs is recommended when the cancer is in the lymph nodes. For rectal cancer, chemotherapy is combined with radiation and often given to stage II cancers also. When used with preoperative radiation, part of the chemotherapy is given before surgery and the rest given after surgery. The most common drugs used are a combination of Fluorouracil (5-FU) and levamisole or leucovorin.

Calcium Sources

It is known that not all calcium sources are equal in terms of bioavailability and absorption. The preferred form is calcium carbonate, which contains the highest amount of absorbable calcium, 40% elemental calcium. Calcium carbonate is cheap, readily available and easily compacted to make a tablet with greater calcium content. Because of the higher elemental calcium content of calcium carbonate, a tablet can be made smaller and can contain a higher concentration of available calcium. Since the tablet can be smaller, it is easier to swallow, especially for older people.

Other sources of calcium for pharmaceutical or supplemental use are calcium gluconate, calcium lactate, dibasic calcium phosphate and calcium citrate and the like. Elemental calcium, is preferably supplied in the range of about 400 and 10,000 mg. The calcium salt content is preferably within the range of 1,000 mg to 25,000 mg, advantageously 1,500 to 3,000 mg.

U.S. Pat. No. 5,741,471 provides a process for the precipitation of discrete prismatic calcium carbonate particles by carbonation of aqueous calcium hydroxide containing a saccharide or polysaccharide, which is useful, inter alia, in pharmaceutical applications.

Additional Components with Calcium

In addition to a calcium salt, a composition for administration in accordance with the invention may contain trace or substantial amounts of other active ingredients. For example, Vitamin D, critical in the role of calcium absorption, can be added in the range between 50 I.U., and 800 I.U. The preferred range is between 200 to 400 I.U.

Preferably one or more of boron, copper, magnesium, manganese and zinc is supplied. The mineral preferably comprises a boron compound or a combination of a boron compound with other minerals. The anions for the minerals can be oxide, phosphate, chloride, sulfate, nitrate, or the like.

The preferred amounts of the mineral supplements are:

boron compound from 50 to 3,000 micrograms;

copper compound from 0.10 to 5.0 mg;

magnesium compound from 10 to 150 mg;

manganese compound from 3 to 10 mg; and, zinc compound from 3 to 25 mg.

Pharmaceutical Compositions and Dosages

As a general statement, the total weight of the dosage form is preferably less than about 5.0 g. In the preferred embodiment (calcium carbonate), the dosage form is equal to or less than about 3.0 g.

The present formulation may also include preservatives such as benzoic acid and salts thereof, butylated hydroxyanisole, butylated hydroxytoluene, sulfur dioxide and the like; food grade emulsifiers such as lecithin, mono- and diglycerides of long chain fatty acids, and propylene glycol esters; and pharmaceutically acceptable carriers and excipients, which are known to those skilled in the art.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The phrase "therapeutically effective amount" or "dose . . . that is effective" is used herein to mean a dose or an amount sufficient to reduce the risk of carcinogenesis, such as but not limited to polyp formation, recurrent adenoma, and development of a carcinoma. Preferably, the risk is reduced by a statistically significant amount, e.g., with an acceptable value for "p". For example, the risk of carcinogenesis may be reduced by at least about 10 percent, preferably by at least 25 percent, more preferably by at least 50 percent, and most preferably completely. Alternatively, a therapeutically effective amount is sufficient to cause an improvement in a clinically significant condition in the host, such as recurrent adenoma.

Formulations

The present formulation may be in oral solid dosage form for example a tablet, capsule, lozenger, chewable tablet or bulk powder. The tablet, capsule or lozenger may contain suitable binders, lubricants, diluents, disintegrating agents, coloring agents, flavoring agents, flow-inducing agents and melting agents which are known to those skilled in the art.

The present formulation may also be in a liquid dosage form which includes an emulsion and suspension. The liquid dosage form may contain, for example, suitable solvents, preservatives, emulsifying agents, suspending agents, diluents, sweeteners, melting agents, and coloring and flavoring agents, which are known to one skilled in the art.

It is preferred to administer the composition of the present invention in the form of tablets; however, any form of oral administration can be used.

The solid dosage form may have a film coating to protect the ingredients from moisture, oxygen or light and to mask any undesirable taste or appearance. Suitable coating agents include cellulose, hydroxy-propylmethylcellulose, cellulose phthalate, methacryulic copolymer and shellac. An enteric coating may be employed, as well as coloring agents for identification and, if desired, the solid form may be polished with a waxy composition, such as carnuba wax.

For example, calcium supplement compressed tablets are well known to the art and commonly contain tricalcium phosphate or a mixture thereof with dicalcium phosphate, a binder such as microcrystalline cellulose, a disintegrant such as sodium starch glycolate or croscarmellose sodium, and a lubricant such as magnesium stearate (see, for example, Kanig et al, International Application Published Under The Patent Cooperation Treaty (PCT), International Publication No. WO 81/02521, published Sep. 17, 198 1, and Gerard European Patent Application Publication No. 54333, published Jun. 23, 1982). The calcium phosphate can be of commercial compacted grade. A suitable compacted grade of tricalcium phosphate is marketed by Stauffer Chemical Company of Westport, Conn. U.S.A. as TRI-TAB.RTM. containing about 37.5% elemental calcium by weight.

Various calcium formulations have been described in patents. For example, U.S. Pat. No. 5,817,351 describes liquid beverages for supplementation of dietary calcium. The beverages of this invention use calcium glycerophosphate as the source of calcium, acidulants, vitamin C and optionally, vitamin D. U.S. Pat. No. 5,780,081 discloses a fortified foodstuff comprising a fortifying amount of a complex of calcium and a hydrolyzed polysaccharide. U.S. Pat. No. 5,766,330 discloses a method for forming a dry powder of insoluble calcium salts and protein from an aqueous composition, e.g., for use in food supplements. U.S. Pat. No. 5,698,222 provides a calcium supplement in solid form contains calcium glycerophosphate, vitamin D and vitamin C. U.S. Pat. No. 5,468,506 provides a concentrated bioavailable calcium source containing a) soluble calcium; b) an edible acid component; and c) sugar. U.S. Pat. No. 4,851,221 provides a liquid calcium supplementation from readily soluble mixtures of citric acid and one or more calcium compounds selected from the group consisting of calcium hydroxide, calcium carbonate and calcium oxide, which may be used, for example, as a powder for making an "instant" beverage. U.S. Pat. No. 4,781,925 discloses a calcium supplement compressed tablet containing tricalcium phosphate with croscarmellose sodium as a disintegrant and sodium lauryl sulfate.

Dosage Regimen

Any dosage regiment that provides an therapeutically effective amount of elemental calcium can be used in the practice of the invention. As noted above, preferably the calcium is administered orally, but any acceptable route of administration can be employed. Similarly, in a specific embodiment, infra, the calcium compound is administered twice daily, preferably with a meal. However, the daily dosage can be provided once a day, twice daily, three times daily, with every meal, etc. Alternatively, a sustained release dosage form can be used, which may provide for administration of a composition comprising the calcium compound less frequently than daily.

The following example is for illustrative purposes and is not to be construed as limiting the invention.

EXAMPLE

Clinical Evaluation of Calcium Intake to Protect Against Colorectal Carcinogenesis To clarify the effect of calcium intake on colorectal carcinogenesis, we conducted a clinical trial of the effect of supplementation with calcium carbonate on the recurrence of colorectal adenomas. We hypothesized that subjects randomized to calcium would have a reduced risk of any recurrent adenoma as well as reduced numbers of adenomas.

Methods

The Calcium Polyp Prevention Study involved six clinical centers: the Cleveland Clinic Foundation, Dartmouth-Hitchcock Medical Center, the University of Southern California/Southern California Permanente Medical Group, the University of Iowa, University of Minnesota, and the University of North Carolina. Dartmouth was the coordinating center and the University of Minnesota was the pathology center. Human subjects committees at each center approved the study protocol; an independent safety and data monitoring committee reviewed the study semi-annually.

Staff at each clinical center monitored colonoscopy and pathology records at associated endoscopy units to identify patients with at least one histologically-confirmed large bowel adenoma removed within three months of recruitment, and with the entire large bowel mucosa subsequently examined and judged free of remaining polyps. Eligible patients were less than eighty years old, in good health, and without a history of familial polyposis, invasive large bowel cancer, malabsorption syndromes, or any condition which might be worsened by supplemental calcium. We aimed to randomize 860 subjects to have 80% power to detect a 25% reduction in adenoma recurrence.

We reviewed data from 2,918 apparently eligible patients. We were unable to contact 233, 1,066 declined participation, 510 were found to be ineligible, and 1 patient did not enroll for unknown reasons. After informed consent, the remaining 1,118 patients began a three-month placebo run-in period to assess adherence to the study regimen of one tablet twice per day with meals. After the run-in, 930 patients had taken at least 80% of their prescribed tablets, wished to continue the study, and were considered appropriate for randomization. We assigned these subjects to calcium or placebo using computer-generated random numbers, blocking by study center. Study tablets contained 3000 mg of calcium carbonate (1200 mg of elemental calcium); or, an identical-appearing cellulose/sucrose placebo. The trial was double-blind; neither subjects nor study staff were told the subjects' treatment assignments.

Subjects received two follow-up colonoscopies as part of their routine clinical care, generally by the same physician who conducted the qualifying exam. The first follow-up examination was planned for approximately one year after the qualifying colonoscopy (about nine months after randomization), and a second follow-up examination was planned for thirty-six months after that. Large bowel endoscopy was otherwise discouraged unless clinically indicated (e.g., for rectal bleeding). Follow-up examinations were considered "adequate" if the entire large bowel mucosa was visualized, and no polyps remained at the end of the procedure. We designated the time from randomization to the first follow-up exam as the first study interval, and the period after the first follow-up exam up to (and including) the second follow-up colonoscopy as the second study interval.

At each colonoscopy, the endoscopist recorded the size and location of all mucosal lesions, using standard clinical technique. By protocol, all polyps were biopsied and removed, and their histology reviewed by the study pathologist who classified them as neoplastic (adenoma) or non-neoplastic (hyperplastic polyp, lymphoid follicle, etc.) The study pathologist also reviewed polyps on the qualifying endoscopy for a 25% sample of subjects. The reviewing pathologist and the clinical center reading agreed as to presence or absence of neoplasia for 2,349 (92%) of the 2,541 specimens reviewed. In cases of disagreement, we accepted the study pathologist's diagnosis.

At enrollment and at the time of each of the two follow-up colonoscopies, we obtained venous blood specimens in mineral-free tubes. Serum was initially stored at –20° C. or lower, pending shipment to Dartmouth for storage at –70° C. until analysis. At enrollment and the end of the study, we also assessed subjects' diet with a validated food frequency questionnaire (Block et al., Am. J. Epidemiol., 124:453–69, 1986). Every six months, we sent patients questionnaires regarding adherence to study agents; use of medications, over-the-counter drugs and nutritional supplements; and the occurrence of symptoms, illnesses, and hospitalizations. Recruitment into the study began in November 1988 and ended in April 1992. Follow-up ended in December 1996.

The primary endpoint of the trial was the proportion of subjects having at least one adenoma detected during the second study interval, i.e., after the first follow-up colonoscopy, up to and including the second follow-up examination (including adenomas detected during interim endoscopies). This choice of end-point had two advantages: it provided for the removal of adenomas overlooked at the qualifying colonoscopy (thus, minimizing the numbers of polyps present at the start of the main risk period), and allowed for a latent period of calcium action. If a subject did not have the follow-up examinations as planned, we accepted the two clinically-indicated colonoscopies at least one year apart that provided the longest follow-up interval.

For our statistical analyses, we compared proportions using Fisher's exact test, and measured data using t-tests or rank tests (Snedecor and Cochran, Statistical Methods, Seventh Edition, Ames: Iowa State University Press, 1980). Our main analysis considered two related outcomes: whether subjects in the two treatment groups had different probabilities of at least one adenoma, and whether the average numbers of adenomas in the two groups differed. To address the first issue, we used overdispersed log-linear quasi-likelihood models programmed in SPlus (Seattle) to provide unadjusted and adjusted estimates and confidence intervals for the relative risk of at least one recurrent adenoma (McCullagh and Nelder, Generalized Linear Models (Second Edition), Chapman-Hall, 1989). Similar models (with variance proportional to the mean) were used to analyze the ratios of the average number of adenomas in the two treatment groups (McCullagh and Nelder, supra). Co-variates included age (linear term), gender, the lifetime number of adenomas before study entry, clinical center, and the length of the surveillance interval. Possible interactions were considered using product interaction terms. Subgroup analyses included investigation of subjects above and below the median of the calorie-adjusted intake (Willet, Nutritional Epidemiology, Oxford University Press, 1990) of selected nutrients. To assess possible distortions introduced by subjects who did not complete the study, we also performed sensitivity analyses by imputing recurrence patterns for these subjects to determine outcomes that would have altered our conclusions, had they been observed. All P-values were two-sided.

Results

We randomized 930 subjects whose characteristics are summarized in Table 1; there were no appreciable differences between the two treatment groups in demographic characteristics, dietary patterns, or adenoma history. The mean age (±SD) was 61±9 years, and 72% were men. Most subjects had had only one or two adenomas removed from the large bowel before entering the study. The mean estimated diameter of the largest qualifying adenoma was 0.7±0.6 cm; in the sample sent for pathological review, 99% had mild/moderate atypia. The mean estimated daily dietary intake of calcium at study entry (877±437 mg per day) was similar in the two study groups, and less than three quarters of the amount later provided as supplements by the study intervention. Fewer than 3% of subjects were taking calcium supplements at the start of the trial; all agreed to discontinue them during the study.

TABLE 1

Demographic and clinical characteristics at entry of the subjects enrolled in the Calcium Polyp Prevention Trial

|  | All Randomized Subjects | | Subjects who completed the study | |
|---|---|---|---|---|
|  | Placebo N (%) | Calcium N (%) | Placebo N (%) | Calcium N (%) |
| Total | 466 (100) | 464 (100) | 423 (100) | 409 (100) |
| Sex | | | | |
| Male | 327 (70.2) | 345 (74.4) | 296 (70.0) | 302 (73.8) |
| Female | 139 (29.8) | 119 (25.6) | 127 (30.0) | 107 (26.2) |
| Mean Age (years) | 61.0 ± 9.1* | 61.0 ± 9.1 | 60.9 ± 9.0 | 60.7 ± 8.8 |
| Study Center | | | | |
| Cleveland Clinic | 72 (15.5) | 71 (15.3) | 70 (16.6) | 67 (16.4) |
| Dartmouth | 85 (18.2) | 72 (15.5) | 76 (18.0) | 62 (15.2) |
| University of Iowa | 87 (18.7) | 86 (18.5) | 79 (18.7) | 74 (18.1) |
| University of Minnesota | 81 (17.4) | 85 (18.3) | 75 (17.7) | 72 (17.6) |
| University of North Carolina | 64 (13.7) | 59 (12.7) | 56 (13.2) | 51 (12.5) |
| University of Southern California | 77 (16.5) | 91 (19.6) | 67 (15.8) | 83 (20.3) |
| Mean Number of Prior Adenomas[1] | 2.6 ± 2.8 | 2.4 ± 2.5 | 2.6 ± 2.9 | 2.5 ± 2.6 |
| Mean Daily Caloric Intake (Kcal)[§] | 2010 ± 756 | 2040 ± 761 | 2011 ± 742 | 2032 ± 756 |
| Mean Total Daily Fat Intake (gms)[§] | 88.1 ± 42.9 | 87.2 ± 41.3 | 87.9 ± 42.2 | 86.1 ± 40.5 |
| Mean Dietary Fiber Intake (mg)[§] | 16.2 ± 7.8 | 16.6 ± 8.0 | 16.4 ± 8.0 | 16.7 ± 8.0 |
| Mean Dietary Calcium Intake (mg)[§] | 865 ± 423 | 889 ± 451 | 866 ± 421 | 893 ± 451 |
| Taking Supplemental Calcium | 13 (2.8) | 11 (2.4) | 12 (2.8) | 11 (2.7) |

*Mean ± standard deviation
[1]Lifetime number of colorectal adenomas found and removed before randomization.
[§]Dietary information was missing for 10 placebo and 13 calcium subjects.

Of the 930 randomized subjects, 832 (89%) completed two follow-up colonoscopies (Table 2). We could not include 98 subjects (43 placebo and 55 calcium) in the main analyses: 47 had died, 25 no longer wished to participate, 18 could not be examined because they were too ill or had moved, and 8 dropped out for unknown reasons. In addition to the study-mandated colonoscopies, an interval colonoscopy or sigrnoidoscopy was performed in the main risk period (second study interval) in 86 (10%) of the patients. The proportions of subjects with an inadequate study colonoscopy or with an interim endoscopy did not differ substantially between treatment groups (Table 2).

TABLE 2

Cooperation of Study Subjects with Trial Examinations

|  | Placebo (N %) | Calcium N (%) |
|---|---|---|
| Randomized Subjects | 466 (100) | 464 (100) |
| Died | 22 (4.7) | 25 (5.4) |
| Dropped out: lost interest | 11 (2.4) | 14 (3.0) |
| Dropped out: ill or moved | 8 (1.7) | 10 (2.2) |
| Dropped out: other or unknown reasons | 2 (0.4) | 6 (1.3) |
| Received first follow-up colonoscopy | 459 (98.5) | 454 (97.8) |
| Mean length of 1$^{st}$ surveillance interval (months) | 13.1 ± 0.18* | 13.6 ± 0.26 |
| Interim endoscopy during 1$^{st}$ surveillance interval[1] | 5 (1.1) | 14 (3.1)** |
| Inadequate 1$^{st}$ follow-up colonoscopy[1] | 21 (4.6) | 22 (4.9) |
| Received 2$^{nd}$ follow-up colonoscopy | 423 (90.8) | 409 (88.2) |
| Mean length of 2$^{nd}$ surveillance interval (months) | 36.6 ± 0.16 | 36.9 ± 0.18 |
| Interim endoscopy during 2$^{nd}$ surveillance interval[1] | 51 (12.1) | 35 (8.6) |
| Inadequate 2$^{nd}$ follow-up colonoscopy[1] | 29 (6.9) | 35 (8.6) |

*Mean ± standard error.
**P for difference in proportions = 0.04
[1]Proportions of subjects receiving the respective follow-up examinations.

Self-reported adherence to the study regimen gradually declined during the trial (Table 3). Nevertheless, even during the fourth year, over 80% of living subjects took study agents 90–100% of the time, and a further 7% took them 50–89% of the time. Use of supplemental calcium was reported at least once by only 19 (2%) patients during the study of (9 placebo, 10 calcium).

TABLE 3

Self-reported adherence to study treatment, according to treatment assignment and year on study

|  | Placebo | | Calcium | |
|---|---|---|---|---|
| % of Tablets Taken | N | % subjects | N | % subjects |
| Year 1 | | | | |
| 90–100% | 409 | 88.0% | 393 | 85.3% |
| 50–89% | 42 | 9.0% | 30 | 10.9% |
| <50% | 14 | 3.0% | 18 | 3.9% |
| Year 2 | | | | |
| 90–100% | 373 | 80.6% | 371 | 81.5% |
| 50–89% | 52 | 11.2% | 44 | 9.7% |

TABLE 3-continued

Self-reported adherence to study treatment, according to treatment assignment and year on study

| % of Tablets Taken | Placebo N | Placebo % subjects | Calcium N | Calcium % subjects |
|---|---|---|---|---|
| <50% Year 3 | 38 | 8.2% | 40 | 8.8% |
| 90–100% | 377 | 83.0% | 358 | 79.7% |
| 50–89% | 33 | 7.3% | 39 | 8.7% |
| <50% Year 4 | 44 | 9.7% | 52 | 11.6% |

TABLE 4

Numbers of subjects with any adenoma recurrence, relative risks of at least one recurrence, and ratios of the average numbers of adenomas, according to treatment assignment

| | TREATMENT GROUP PLACEBO | | TREATMENT GROUP CALCIUM | | Relative risk for 1 or more adenomas* | Ratio of the mean number of adenomas* |
|---|---|---|---|---|---|---|
| | % with one or more adenomas | Mean number of adenomas | % with one or more adenomas | Mean number of adenomas* | | |
| Subjects who have completed the study (423 Placebo, 409 Calcium) | | | | | | |
| 1st Study Interval§ | 32.6% | 0.60 | 25.2% | 0.43 | 0.78 (0.63 to 0.96) | 0.75 (0.58 to 0.96) |
| 1st Study Exam | 32.6% | 0.59 | 24.4% | 0.40 | 0.75 (0.61 to 0.94) | 0.70 (0.54 to 0.89) |
| 2nd Study Interval§ | 37.6% | 0.73 | 31.1% | 0.55 | 0.81 (0.67 to 0.99) | 0.76 (0.60 to 0.96) |
| 2nd Study Exam | 35.7% | 0.62 | 30.1% | 0.51 | 0.83 (0.68 to 1.01) | 0.83 (0.65 to 1.05) |
| 1st or 2nd Study Interval§ | 52.2% | 1.32 | 44.7% | 0.98 | 0.85 (0.74 to 0.98) | 0.75 (0.62 to 0.90) |
| Subjects who had at least one endoscopy (459 Placebo, 454 Calcium) | | | | | | |
| 1st or 2nd Interval§ | 50.5% | 1.26 | 43.2% | 0.92 | 0.85 (0.74 to 0.98) | 0.75 (0.63 to 0.90) |
| Study Exams | 50.1% | 1.25 | 42.3% | 0.86 | 0.84 (0.73 to 0.97) | 0.77 (0.64 to 0.91) |

*Risk ratio of at least one adenoma and ratio of the mean numbers of adenomas. Both estimates adjusted for age, gender, clinical center, number of previous adenomas, and length of follow-up interval.
§First study interval, randomization to first follow-up colonoscopy; second study interval, after first follow-up colonoscopy up to and including second follow-up colonoscopy.

TABLE 3-continued

Self-reported adherence to study treatment, according to treatment assignment and year on study

| % of Tablets Taken | Placebo N | Placebo % subjects | Calcium N | Calcium % subjects |
|---|---|---|---|---|
| 90–100% | 358 | 81.7% | 346 | 79.0% |
| 50–89% | 31 | 7.1% | 34 | 7.8% |
| <50% | 49 | 11.2% | 58 | 13.2% |

Note: Numbers of subjects may not sum to 930 because of drop-outs and missing data.

Among the 832 subjects who completed the study, at least one colorectal adenoma was diagnosed during the main risk period (the second study interval) in 127 (31.1%) calcium patients and 159 (37.6%) placebo patients (Table 4). The mean size of the largest adenoma was equal in the two groups (0.4 cm; P=0.43), but more adenomas were found in the placebo group (mean 0.73 versus 0.55 for placebo, P=0.03). The unadjusted risk ratio for at least one adenoma was 0.83) 95% confidence interval 0.68 to 1.00; P=0.05); after adjustment, this was 0.81 (95% confidence interval 0.67 to 0.99; P=0.04). The unadjusted ratio of the average number of adenomas was 0.75 (95% percent confidence interval 0.58 to 0.97; P=0.03); this was 0.76 (95% confidence interval 0.60 to 0.96; P=0.02) after adjustment. During the main risk period, invasive large bowel cancer was found in four subjects (3 placebo, 1 calcium), and no adenomas with severe atypia were removed (P for differences in proportions with severe atypia or cancer=0.62). Analysis of adenomas detected on the second follow-up examination (excluding findings on interval endoscopies) yielded identical results (Table 4).

A similar calcium effect was found during the first study interval. Among the subjects who completed the trial, at least one adenoma was noted in the period up to and including the first follow-up exam in 103 (25%) calcium subjects and 138 (33%) placebo subjects (Table 4). The unadjusted risk ratio for at least one adenoma in this early interval was 0.77 (95% confidence interval 0.62 to 0.96; P=0.02); the unadjusted ratio of the average numbers of adenomas was 0.73 (95% confidence interval 0.54 to 0.97; P=0.03). These estimates were virtually unchanged after multivariate adjustment. Analysis of adenomas detected on the first follow-up examination yielded similar findings. At or before the first follow-up, invasive cancer was found in four patients (2 calcium, 2 placebo), and an adenoma with severe atypia was removed from one participant in each treatment group.

A total of 913 subjects had at least one study colonoscopy. The unadjusted risk ratio of at least one adenoma after randomization was 0.85 (95% confidence interval 0.74 to 0.98; P=0.03); the corresponding ratio of the average numbers of adenomas was 0.74 (95% confidence interval 0.59 to 0.92; P=0.0006). Restriction of the analysis to adenomas detected on study follow-up examinations, and adjustment for age, clinical center, sex, length of the surveillance interval, and number of previous adenomas, left these estimates unchanged (Table 4).

We also assessed whether the effect of calcium supplementation differed according to the size or location of the adenomas. During the main (i.e., the second) study interval, an adenoma 0.5 cm or greater was found in 120 subjects (63 placebo and 57 calcium); the unadjusted risk ratio for at least one adenoma of this size versus no adenomas was 0.87 (95% confidence interval 0.63 to 1.21; P=0.70). In 166 subjects, the largest adenoma was less than 0.5 cm (96 placebo and 70 calcium); the corresponding unadjusted risk ratio was 0.75 (95% confidence interval 0.57 to 0.98; P=0.03). During the second interval, 144 patients had at least one adenoma in the splenic flexure or more distally, and 200 had at least one adenoma proximal to the splenic flexure. Calcium had a similar effect on adenoma recurrence in both regions of the bowel (data not shown).

The sensitivity analysis indicated that it is extremely unlikely that outcomes from the 98 subjects who did not complete the study would have nullified our findings had they been available. Among these subjects recurrent adenomas would had to have been at least twice as frequent in the calcium group than in the placebo group to remove the statistical significance of the overall calcium effect.

There was no evidence of modification of the calcium effect by age, gender, or baseline dietary intake of calcium, fat or fiber (data not shown). The effect of calcium was non-significantly stronger among subjects who reported taking all their study agents and among those who did not report any use of aspirin or other non-steroidal anti-inflammatory drugs (data not shown).

Medical complaints and complications were not associated with treatment assignment. Similar proportions of calcium and placebo subjects were hospitalized for any reason, were hospitalized with cancer, or stopped treatment because of perceived side effects (Table 5). The frequency of digestive symptoms (including constipation) did not differ materially between the two treatment groups. Two calcium patients and one placebo patient diagnosed with definite or probable urinary stones.

TABLE 5

Medical events after randomization, according to treatment group assignment

|  | Placebo | N (%) | Calcium | N (%) |
|---|---|---|---|---|
| Number of Subjects | 466 | (100) | 464 | (100) |
| Deaths | 22 | (4.7) | 25 | (5.4) |
| Subjects Hospitalized | 164 | (35.2) | 172 | (37.1) |
| All cancer | 21 | (4.5) | 15 | (3.2) |
| Cardiac disease | 46 | (9.9) | 50 | (10.8) |
| Stroke | 11 | (2.4) | 12 | (2.6) |
| Gastrointestinal disease | 32 | (6.9) | 38 | (8.2) |
| Other | 114 | (24.5) | 126 | (27.2) |
| Stopped treatment because of perceived toxicity | 13 | (2.8) | 12 | (2.6) |

Note: There were no statistically significant differences in the proportions between treatment groups.

Discussion

In this randomized clinical trial, assignment to calcium supplementation was associated with a statistically significant reduction in the risk of recurrent adenomas. The reduced risk was modest, but became apparent as early as the first colonoscopic follow-up, after approximately nine months. There was no indication of a greater effect among subjects with low baseline dietary intake of calcium or high intake of fat. The intervention was well-accepted and without toxicity.

Epidemiological data regarding the association between dietary calcium and the risk of colorectal cancer have varied considerably, but in aggregate are consistent with the effect we observed (Blergsma-Kadijk et al., supra; Martinez and Willet, supra). Many studies (Slattery et al., Am. J. Epidemiol., 1988, 125:505–514; Whittemore et al., J. Natl. Cancer. Inst., 1990, 82:915–926; Garland et al., Lancet, 1985, 1:307–9; Bostick et al., Am. J. Epidemiol., 1993, 137:1302–17; Kearney et al., Am. J. Epidemiol., 1996, 43:907–917; and, Martinez et al., J. Natl. Cancer Inst., 1996, 88:1375–1382) found at least suggestions of an inverse association, but others found no relation (Graham et al., Am. J. Epidemiol., 1988, 128:490–503; Boutron et al., Brit. J. Cancer, 1996, 74:145–151), or even the possibility of an increased risk with higher intake (Kampman et al., Cancer Res., 1993, 54:3186–3190; Pritchard et al., Cancer Epidemiol. Biomarkers Prev., 1996, 5:897–900). Investigations of calcium intake and the risk of colorectal adenomas have also been conflicting (Boutron et al., supra; Little et al., Brit. J. Cancer, 1993, 67:177–18; Kampman et al., Am. J. Epidemiol., 1994, 139:16–29; Tseng et al., Am. J. Epidemiol., 1996, 144:1005–1014) as have studies that considered calcium supplementation separately (Bostick et al., supra; Kampman et al., supra; Neugut et al., Cancer, 1996, 78:723–8).

These mixed findings may reflect the difficulties of dietary epidemiology. The effects of calcium intake are likely to be confounded by factors such as intake of calories,-dietary fat and phosphate, and perhaps, use of vitamin/mineral supplements, aspirin, or other agents with anti-carcinogenic effects. Moreover, the measurement error inherent in dietary assessment would tend to obscure any association between calcium intake and the risk of neoplasia (Willet, supra).

Extensive animal research supports an anti-neoplastic effect of calcium in the large bowel. Calcium inhibits the mucosal injury and hyperproliferation induced by bile acids or carcinogens (Pence, supra), and most studies that used high-fat diets reported lower tumor incidence with supplementations (Pence, supra; Pence and Buddingh, supra).

Effects of calcium have been absent or less pronounced among animals fed low-fat diets (McSherry et al., Cancer Res., 1989, 49:6039–43; Sitrin et al., Cancer Res., 1991, 51:5608–5613). One experimental study suggested that dietary calcium particularly inhibited tumors with ras mutations (Llor et al., Cancer Res., 1991, 51:4305–4309), a recent epidemiological study reported similar effects (Bautista et al., Cancer Epidemiol. Biomarkers Prev., 1997, 6:57–61).

Previously published trials of calcium supplementation have focused on biological markers; some of these have supported the hypothesis that calcium may act through precipitation of bile acids or stool fatty acids, perhaps in complexes with calcium phosphate (Van der Meer, et al., Cancer Lett., 1997, 114:75–83). Calcium supplementation has been observed to reduce cytotoxicity of fecal water reduce the proportion of secondary bile acids in the bile acid pool, and reduce fecal bile acid concentrations (Van der Meer et al., supra; Cats et al., J. Natl. Cancer Inst., 1995, 87:598–603; Lupton et al., J. Nutr., 1996, 126:1421–1428; Alberts et al., J. Natl. Cancer, Inst., 1996, 88:81–92). However, other investigations did not suggest such benefits, reporting no change in the concentration of bile acids in the water phase of stool (Lapré et al., Cancer Res., 1993, 53:248–253; Stern et al., Surgery, 1990, 108:528–33), or an actual increase (Gregoire et al., Gut, 1989, 30:376–382; Alder et al., Am. J. Epidemiol., 1993, 138:804–814). Studies of the effect of calcium on rectal mucosal proliferation have been conflicting (Cats et al., supra; Stern et al., supra; Gregoire et al., supra; Lipkin and Newmark, N. Engl. J. Med., 1985, 313:1381–1384; Wargovich et al., Gastroenterology, 1992, 103:92–97; Baron et al., J. Natl. Cancer Inst., 1995, 87:1303–7; Bostick et al., J. Natl. Cancer Inst., 1995, 87:1307–15; Armitage et al., Brit. J. Cancer, 1995, 71:186–190).

Our results are based on adenoma recurrence and do not directly address whether calcium affects the progression of adenomas to invasive cancer or the risk of a first adenoma. The similarity of risk factors for colorectal cancer, recurrent adenomas and incident adenomas (Peipins and Sandler, Epidemiol. Rev., 1994, 16:273–297) provides reassurance regarding the relevance of our finding for colorectal cancer itself. On the other hand, the calcium effect may have been weaker for large adenomas than for small ones, consistent with a limited efficacy for more advanced tumors. The suppressive effect of calcium was seen less than a year after randomization, and the effect did not become stronger with time. Conceivably, increasing efficacy was counterbalanced by decreasing compliance.

Our data suggest that calcium carbonate may have chemopreventive activity against colorectal neoplasia. The effect we found is consistent with epidemiological data and is supported by a large body of experimental data in humans and in animals. Since the toxicity of this simple and inexpensive agent appears to be minimal, and since it may have other benefits (e.g., reduction of the risk of osteoporosis (Dawson-Hughes et al., N. Engl. J. Med., 1997, 337:670–676)), its risk-benefit balance is likely to be favorable. However, before a general recommendation regarding large-scale calcium supplementation can confidently be made, it would be desirable to confirm these findings, obtain more information about effects on frank carcinoma or sever dysplasia, and document the risk/benefit balance in various population groups.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

Patents, patent applications, and publications are cited throughout this application, the disclosures of which are incorporated herein by reference in their entireties.

What is claimed is:

1. A method for promoting colon health in a human subject comprising administering a dose of elemental calcium to the subject that is effective to promote colon health.

2. The method according to claim 1, wherein the dose of elemental calcium ranges from about 1 mg/kg/day to about 100 mg/kg/day.

3. The method according to claim 2, wherein the dose of elemental calcium ranges from about 1 mg/kg/day to about 50 mg/kg/day.

4. The method according to claim 3, wherein the dose of elemental calcium is about 20 mg/kg twice a day.

5. The method according to claim 2, wherein the dose of elemental calcium is about 1200 mg/kg once a day.

6. The method according to claim 2, wherein the dose of elemental calcium is about 1200 mg/kg twice a day.

7. The method according to claim 1, wherein the elemental calcium is provided in a compound selected from the group consisting of calcium carbonate, calcium citrate, calcium hydroxide, calcium phosphate, calcium chlorophosphate, or combinations thereof.

8. The method according to claim 7, wherein the elemental calcium is provided as calcium carbonate.

9. The method according to claim 8, wherein the dose of calcium carbonate ranges from about 20 to about 80 mg/kg twice a day.

10. The method according to claim 9, wherein the dose of calcium carbonate is about 40 mg/kg twice a day.

11. The method according to claim 8, wherein the dose of calcium carbonate is about 3000 mg once a day.

12. The method according to claim 8, wherein the dose of calcium carbonate is about 3000 mg twice a day.

13. The method according to claim 7, wherein the dose of elemental calcium is administered with meals.

\* \* \* \* \*

UNITED STATES PATENT AND TRADEMARK OFFICE
CERTIFICATE OF CORRECTION

PATENT NO. : 6,558,711 B1
APPLICATION NO. : 10/210303
DATED : May 6, 2003
INVENTOR(S) : John A. Baron Page 1 of 1

It is certified that error appears in the above-identified patent and that said Letters Patent is hereby corrected as shown below:

In the Specification

At Column 1, please delete Lines 14 - 17 and insert in its place the following:
--This invention was made with government support under grant numbers CA023108, CA037287, CA046927, and CA053827 awarded by the National Institutes of Health. The government has certain rights in the invention.--

Signed and Sealed this
Sixth Day of October, 2020

Andrei Iancu
*Director of the United States Patent and Trademark Office*

EX PARTE REEXAMINATION CERTIFICATE (10390th)

United States Patent
Baron

(10) Number: US 6,558,711 C1
(45) Certificate Issued: Nov. 10, 2014

(54) COMPOSITION AND METHOD FOR REDUCING THE RISK OF CARCINOGENESIS

(76) Inventor: John A. Baron, Norwich, VT (US)

Reexamination Request:
No. 90/012,939, Aug. 1, 2013

Reexamination Certificate for:
Patent No.: 6,558,711
Issued: May 6, 2003
Appl. No.: 10/210,303
Filed: Aug. 1, 2002

Related U.S. Application Data

(63) Continuation of application No. 09/819,009, filed on Mar. 27, 2001, now Pat. No. 6,488,966, which is a continuation of application No. 09/464,047, filed on Dec. 15, 1999, now Pat. No. 6,251,439.

(60) Provisional application No. 60/115,667, filed on Jan. 13, 1999, provisional application No. 60/112,246, filed on Dec. 6, 1998.

(51) Int. Cl.
| | |
|---|---|
| *A61K 31/19* | (2006.01) |
| *A61K 33/06* | (2006.01) |
| *A61K 33/08* | (2006.01) |
| *A61K 33/42* | (2006.01) |
| *A61K 31/185* | (2006.01) |
| *G06Q 40/00* | (2012.01) |

(52) U.S. Cl.
USPC ............ 424/678; 424/682; 424/686; 424/687

(58) Field of Classification Search
None
See application file for complete search history.

(56) References Cited

To view the complete listing of prior art documents cited during the proceeding for Reexamination Control Number 90/012,939, please refer to the USPTO's public Patent Application Information Retrieval (PAIR) system under the Display References tab.

*Primary Examiner* — Bruce Campell

(57) ABSTRACT

A method for promoting colon health in a subject comprising administering a dose of calcium to the subject that is effective to reduce carcinogenesis. Particularly provided is a method for reducing the risk of recurrence of colorectal adenomas, comprising administering a dose of calcium carbonate effective to promote colon health. In an example, 1200 mg of elemental calcium (supplied in 3000 mg of calcium carbonate) administered once or twice daily resulted in decreased risk of recurrent colorectal adenomas in patients with a history of colorectal adenomas.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 1 is determined to be patentable as amended.

Claims 2-13, dependent on an amended claim, are determined to be patentable.

New claim 14 is added and determined to be patentable.

1. A method for promoting colon health in a human subject comprising administering *to a subject with a history of at least one adenomatous polyp* a dose of *enterically coated* elemental calcium [to the subject that is effective] to promote colon health.

*14. The method according to claim 1, further comprising administering vitamin D.*

\* \* \* \* \*